United States Patent [19]
Stuebe et al.

[11] Patent Number: 5,117,827
[45] Date of Patent: Jun. 2, 1992

[54] APPARATUS AND METHOD FOR AMBULATORY REFLUX MONITORING

[75] Inventors: Thomas D. Stuebe; Paul M. Helmstetter; Charles S. Clark, all of Littleton, Colo.

[73] Assignee: Sandhill Scientific, Inc., Littleton, Colo.

[21] Appl. No.: 603,984

[22] Filed: Oct. 26, 1990

[51] Int. Cl.⁵ .............................................. A61B 5/05
[52] U.S. Cl. .................................................. 128/635
[58] Field of Search ............... 128/635, 642, 721, 760, 128/780, 774; 606/196

[56] References Cited

U.S. PATENT DOCUMENTS

| | | | |
|---|---|---|---|
| 4,474,183 | 10/1984 | Yano et al. | 128/635 |
| 4,608,996 | 9/1986 | Brown | 128/760 |
| 4,774,956 | 10/1988 | Kruse et al. | 128/635 |
| 4,981,470 | 1/1991 | Bonbeck | 128/635 |
| 5,002,055 | 3/1991 | Merki et al. | 128/635 |

*Primary Examiner*—Max Hindenburg
*Attorney, Agent, or Firm*—Townsend and Townsend

[57] ABSTRACT

A system and method for monitoring gastric acid reflux in a patient are described. A system constructed in accordance with the present invention comprises a combination probe including a flexible tube having a pH probe disposed distally and a pressure sensor disposed a known distance proximally, the pH probe for generating pH signals in response to a hydrogen ion concentration, and the pressure sensor for generating pressure signals in response to phasic pressure changes; a display for displaying the pressure signals to aid the positioning of the probe at the LES; and a memory for storing the pH signals. A method of the present invention comprises placing the combination pH/pressure probe in the patient's stomach then withdrawing the probe until the LES respiration phasic pressure is observed from the display. Next, the probe is withdraw a known distance. This positions the pH probe at a specified distance above the LES where reflux may be monitored.

17 Claims, 10 Drawing Sheets

APPARATUS AND METHOD FOR AMBULATORY REFLUX MONITORING

BACKGROUND OF THE INVENTION

The present inventions relates generally to the construction and use of medical monitoring devices. More particularly, the invention relates to an ambulatory monitoring device for measuring gastric acid reflux in a patient.

Gastric acid reflux is a common human ailment arising from the backwash or "reflux" of stomach acid into the esophagus. Mild reflux or "heartburn" is a very common condition experienced by nearly everyone at one time or another. However, prolonged or repeated bathing of the esophagus with gastric acid leads to gastroesophageal reflux disease or "GERD." Left untreated, this condition may progress to esophagitis, esophageal ulceration, stricture, and malignant tumor formation.

Early diagnosis of reflux is an important aspect in the successful treatment and prevention of GERD. While many patients experience heartburn-like symptoms during reflux, it is difficult to quantify the degree of reflux from symptoms alone. Symptoms may even be absent in some patients. Moreover, since reflux mimics cardiac chest pain (and vice versa), the physician must confirm that the symptoms are in fact due to reflux. Thus, in evaluating the patient suspected of having reflux, it is necessary to assess the presence and severity of reflux, nature of refluxant, presence and severity of esophagitis, and pathophysiology of reflux.

The lower esophageal sphincter (LES), in conjunction with the anatomical configuration of the gastroesophageal (G-E) junction, forms an anti-reflux "valve" between the stomach and the esophagus. The LES cannot be identified anatomically as anything but the lower end of the esophagus, i.e., it is virtually indistinguishable from the muscle of the esophagus. Nevertheless, the circular muscle there remains tightly constricted between swallows, thereby preventing the regurgitation of gastric contents into the esophagus. Reflux occurs when the LES-gastric pressure gradient is lost, for example, by a transient or sustained decrease in sphincter tone or by increased intragastric pressure.

Since the mid 1970's, several diagnostic tests have been devised to measure the occurrence of reflux occurring in a patient by measuring acidity above the LES. A simple way of documenting reflux is to first insert a pH probe down the nose or mouth towards the stomach. A low pH reading is observed when the probe reaches the acid-rich stomach. Next, the probe is slowly retracted while monitoring the pH for change. As the probe enters the lesser acidic esophagus, a rise in pH is detected. This location is assumed to be the LES and measurements are taken. Unfortunately, this assumption is more often wrong than right. Thus, the results obtained are unreliable.

A more accurate method of measuring reflux is to place a pH probe a certain or specified distance above the LES. Scoring criteria (for example, the Johnson and DeMeester score) have been established to grade the severity of the reflux based on this technique. However, the technique is reliable only if the pH probe is properly positioned at a known location—a certain distance above the LES. Since the LES is not a clearly defined anatomical structure, it is preferably located by pressure measurements to detect the "high pressure zone" (HPZ). The HPZ location is considered to be the anatomical site of the LES. Thus, a prerequisite to accurately measuring reflux in a patient is determining the correct location of the HPZ.

Locating the HPZ can be done as part of a diagnostic esophageal motility study. Using standard esophageal intubation technique, a probe equipped with a pressure transducer is inserted into the nose or mouth (naso- or oro-esophageal intubation), advanced through the pharynx and esophagus until it reaches the stomach. The pressure transducer, which converts pressure readings into electrical signals, can be recorded on a strip chart recorder.

While observing the recorder, the operator, such as a physician or technician, slowly withdraws the probe from the stomach. As the transducer traverses the HPZ a rise in pressure is noted. At this instance, the depth of the probe is noted. Then the pressure transducer probe is removed from the patient. Next, a pH probe is inserted and advanced to a depth of 5 cm above the LES. The pH probe can be connected to a data collection box or "data logger" which the patient wears for a 24-hour collection period. During this time the pH is frequently measured (typically at 5 seconds intervals) with the values stored in memory. Upon completion of the test, the probe is removed and the data are analyzed.

While this technique is an improvement over prior procedures, it still has several disadvantages. Most reflux patients have low or non-existent LES tone (LES incompetence), thus this technique is unable to accurately determine the LES for these patients. The technique also requires two intubations, i.e., the placement of two probes in succession. Most patients find intubation uncomfortable but tolerable. Some patients, however, such as those with hyperactive gag reflexes, exhibit severe discomfort with intubation. In this latter group, initial intubation is difficult and repeated intubation is impossible. Furthermore, the technique employs hardware which is cumbersome, expensive, and complicated—requiring trained technicians or nurses to operate them—thus making the test expensive.

What is needed is a system which provides a cost effective and accurate method to monitor reflux with minimum inconvenience to the patient. The present invention fulfills these and other needs.

SUMMARY OF THE INVENTION

Twenty-four hour ambulatory pH monitoring of the lower esophagus has become recently important in the medical field. It is useful in diagnosing reflux of acid from the stomach into the esophagus. Left untreated, reflux is accompanied by serious complications. Early diagnosis and treatment is the mainstay of preventing these complications.

The present invention provides for the use of a combination pH and pressure sensing probe connected to a data logger. A system constructed in accordance with the present invention is a combination sensor or probe including a flexible tube having a pH probe disposed distally and a pressure sensor or probe disposed a known distance proximally, the pH probe for generating pH signals in response to a hydrogen ion concentration, and the pressure sensor for generating pressure signals in response to phasic pressure changes—fluctuating or varying pressure states; a display for displaying the pressure signals to aid the positioning of the probe at the LES; and a memory for storing the pH signals.

A method of the present invention includes placing the combination pH/pressure probe in the patient's stomach then withdrawing the probe until the HPZ is located by observing the LES respiration phasic pressure. Next, the probe is withdrawn a known distance. This positions the pH probe at a specified distance above the LES where reflux may be monitored.

The present invention provides the advantage of an accurate method for placing the pH probe based on pressure measurements with a single intubation of the patient and without the need for high cost recording equipment. In addition, since the method of the present invention uses only one intubation, time and money are saved and patient discomfort is reduced.

DESCRIPTION OF THE SPECIFIC EMBODIMENTS

Figure 1:
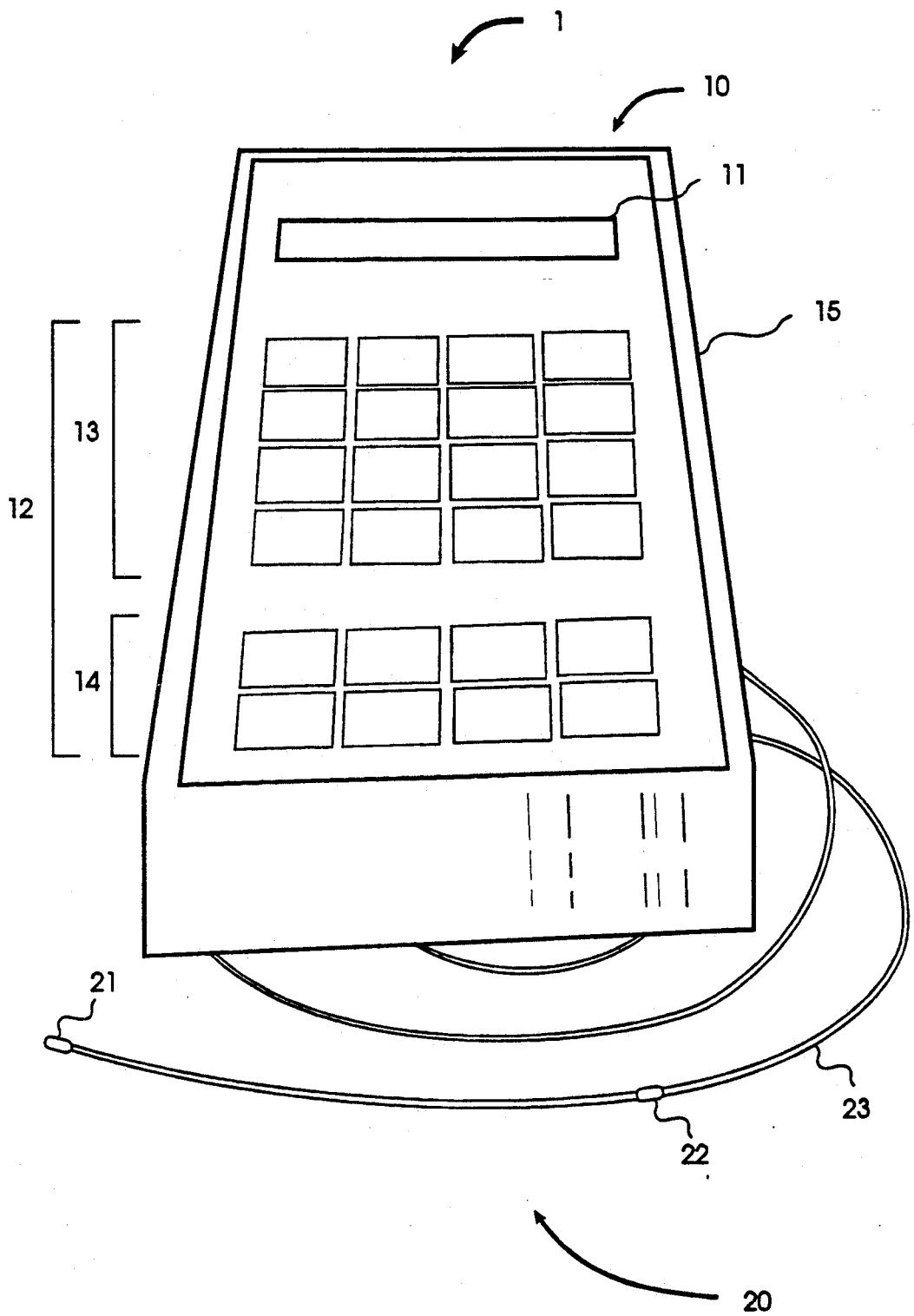
FIG. 1 illustrates the general external appearance of an ambulatory reflux monitoring device constructed in accordance with the principles of the present invention.

Referring now to FIG. 1, an ambulatory reflux monitoring device 1 constructed in accordance with the principles of the present invention includes a pH data logger 10 selectively coupled to a combination pH and pressure sensor probe 20. Data logger 10 is disposed within a portable housing 15 suitable for ambulatory use. Logger 10 is a substantial modification of pH Data Logger, Model RMS-II (Sandhill Scientific, Littleton, Colo.). External features of data logger 10 include a keypad 12 and a display 11, such as a liquid crystal display (LCD). Keypad 12 is further divided into two sets of keys: a first set 13 for entering numerical data and selecting functions and a second set 14 for logging events.

Combination pH and pressure sensor probe 20 includes a flexible tube 23 having a pH sensor point 21 at its distal end. pH probe 21 generates pH signals in response to relative hydrogen ion concentrations. Probe 20 also includes a pressure sensor point or probe 22 along tube 23 for generating pressure signals in response to phasic pressures. As illustrated, pressure sensor probe 22 is positioned proximally. Flexible tube 23 preferably includes distance markings so that its depth may be readily determined relative to teeth or an external nare.

As described thus far, the construction of device 1 is generally conventional. The present invention lies in the provision of pH probe 21 and pressure sensor 22 within the same probe 20, where the linear distance between probes 21, 22 is known. This configuration provides for the accurate positioning of pH probe 21 with a single patient intubation. Additionally, the present invention lies in a method in which the system positions the probe—by measuring the pressure waves from the diaphragm at the LES (the pressure inversion point or PIP).

A PREFERRED EMBODIMENT

Figure 2:
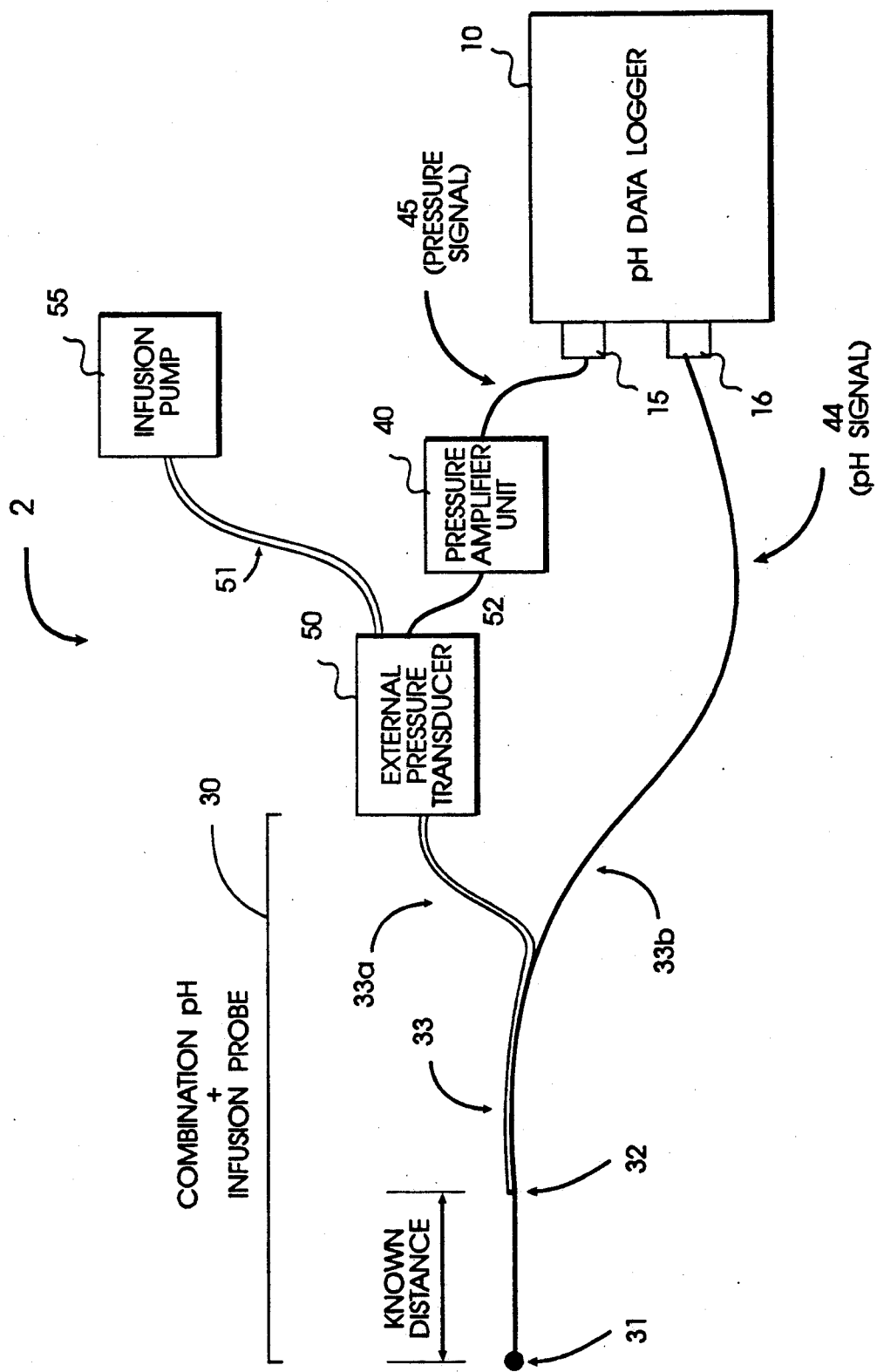
FIG. 2 is a block diagram illustrating a first ambulatory monitoring device constructed in accordance with the principles of the present invention, where an infusion probe is employed to measure pressure.

A preferred embodiment constructed in accordance with the principles of the present invention is a system where probe 20 includes a combination pH and infusion probe. Referring to FIG. 2, this preferred embodiment is illustrated. System 2 includes a combination pH and infusion probe 30 selectively coupled to a pH data logger 10. Probe 30 includes a flexible tube 33 having a pH probe 31 for measuring acidity secured distally and an infusion probe 32 for measuring phasic pressures secured proximally. The distance between probes 31, 32 is fixed at a particular distance. In a preferred embodiment, the distance is 5 cm. Member 33 contains distance markings for easy assessment of depth.

As illustrated, flexible tube 33 is a single channel probe which divides proximally into infusion tube 33a and collinear line 33b. pH probe 31 is coupled to collinear line 33b. pH probe 31 is preferably located at the distal tip so that a bulb-type pH probe may be employed. A bulb-type pH probe is able to measure pH in all directions and thus obtains more representative data.

At a known distance proximal to pH probe 31, infusion probe 32 is coupled to infusion tube 33a. Infusion probe 32 is situated proximally so that it does not remain within the stomach or at the HPZ when pH probe 31 is properly positioned above the LES. Infusion tube 33a is provided with a lumen capable of transporting fluid, such as water or saline. Combination pH and infusion probe 33 is similar in design to Zynetics Model 10-242 Single Channel pH Probe (available from Zynetics of Salt Lake City, Utah).

At its proximal aspect, infusion tube 33a is coupled to an external pressure transducer 50. In turn, external pressure transducer 50 is coupled to infusion pump 55 (e.g., Model APIP-4-4A Infusion Pump from MUI Scientific, Toronto, Canada) via infusion tube 51. Connection of infusion tube 33a to external pressure transducer 50 allows for the measurement of pressure from outside the esophagus by observing the "back pressure" on a column of water provided by infusion pump 55. This technique reduces the size of probe 30, thereby increasing patient comfort. Since an internal pressure transducer is not employed, probe 30 is relatively inexpensive to produce and is disposable. This feature eliminates the threat of communicable diseases and reduces the cost of sterilization.

Responsive to pressures from infusion probe 32, external pressure transducer 50 generates a pressure signal which is transmitted to pressure amplifier unit (PAU) 40 via line 52. PAU 40 serves as an electronic signal conditioning unit to amplify (and process as described hereinbelow) the pressure readings. pH data logger 10 is selectively coupled to PAU 40 at port 15 for receiving a pressure signal via line 45. In a similar fashion, pH data logger 10 is provided with an additional port 16 for selectively coupling to line 33b for receiving a pH signal 44.

Figure 3:
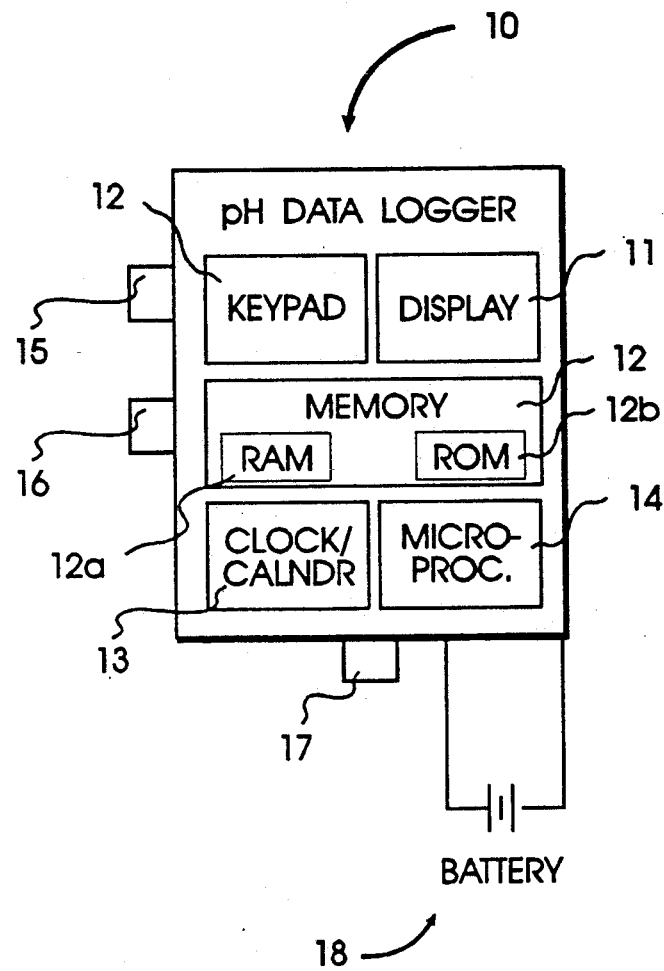
FIG. 3 is a block diagram illustrating a pH data logger constructed in accordance with the principles of the present invention.

Referring now to FIG. 3, the construction of pH data logger 10 is as follows. As illustrated, logger 10 is actually a collection of subunits: keypad 12, display 11, memory 12, microprocessor 14, clock/calendar 13, and ports 15, 16, 17. The subunits are interconnected to permit communication between them. Information enters data logger 10 via keypad 12 and ports 15, 16. The output of information is through display 11 and communication port 17. Display 11 provides information to an operator of the system, for example, by displaying a menu of pressure measure routines. In addition, pressure feedback information is shown on display 11 in response to signals from pressure amplifier 40; this is used to position the pH probe. Communication port 17 is suitable for transmitting information to other systems, for example, a personal computer. Logger 10 is provided with its own battery 18.

Information in logger 10 is stored in a memory 12 having both volatile and non-volatile features. Memory 12 includes a ROM 12b for storing programming instructions and a random-access memory (RAM) 12a for storing pH information received from the patient. Coupled to memory 12 is a microprocessor 14 for receiving and processing the instructions of read-only memory (ROM) 12b. ROM 12b stores a computer program for interpreting pressure signals. In response to pressure signals, microprocessor 14 is programmed to detect phasic variations in pressure. The pressure signals may be represented on display 11 with text, such as a numerical output, or with graphics, such as a bar chart. ROM 12b also includes general routines for directing the mode of system operation. In order to correlate patient data with time, logger 10 includes a clock/calendar 13.

Figure 4:
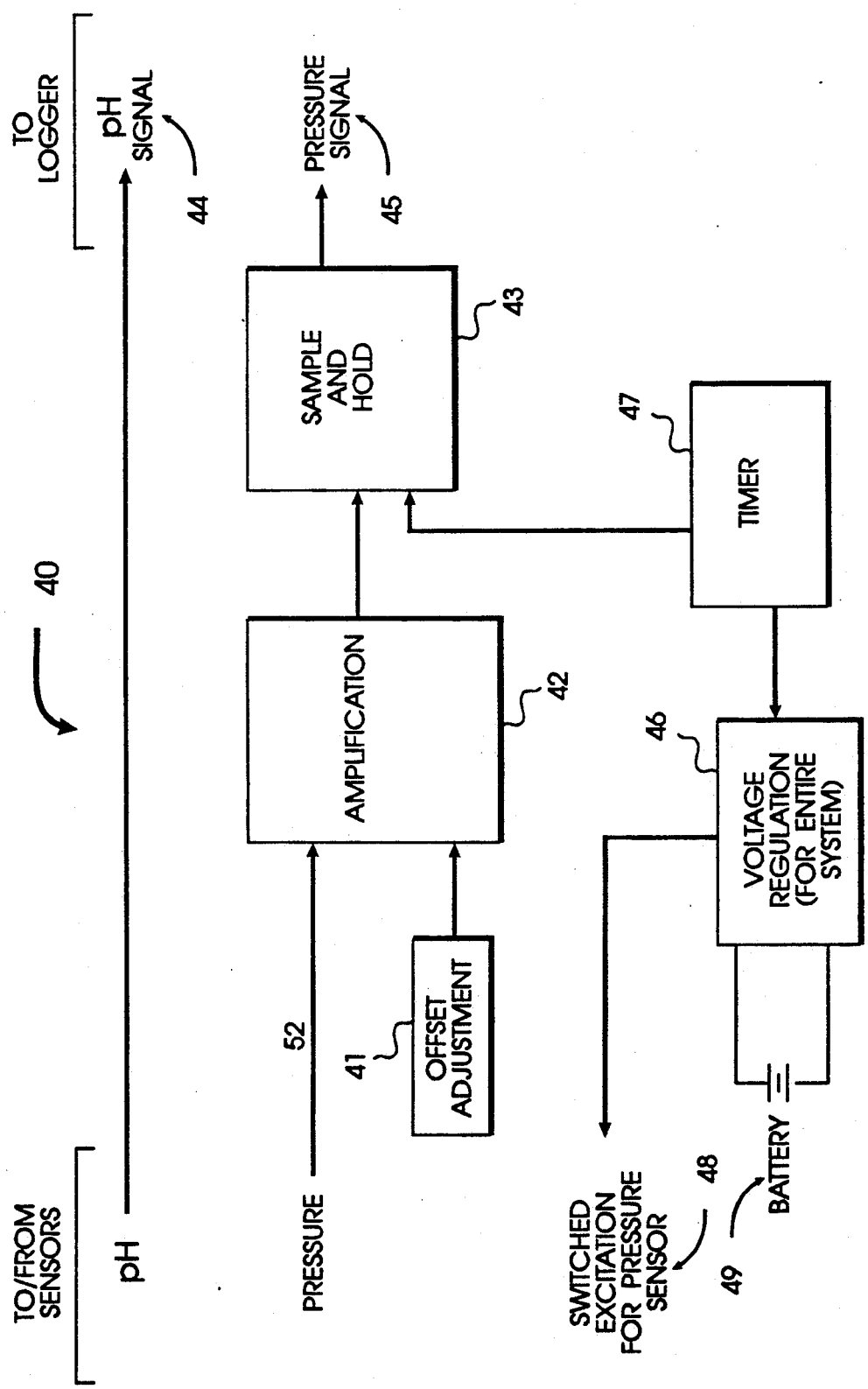
FIG. 4 is a block diagram of a pressure amplifier unit constructed in accordance with the principles of the present invention.

Referring to FIG. 4, pressure amplifier unit (PAU) 40 is further illustrated. PAU 40 includes an amplifier 42 for receiving and amplifying pressure input from line 52. In order to observe the LES's small phasic pressures, the present system must be able to resolve pressures of less than 1 mm HG. However, there may be as much as 15 mm HG of pressure offset between use due to pressor sensor drift, barometric pressure changes, and so forth. Amplifier 42 is coupled to offset adjustment unit 41 which allows the operator to adjust the current output to zero. In particular, offset adjustment unit 41 is an adjustable DC voltage that is subtracted from the pressure signal. This compensates for the aforementioned fluctuations. The adjustment is necessary in order to have sufficient signal gain in amp 42 without saturating it. The adjusted output is sent to sample and hold unit 43.

Sample and hold unit 43 temporarily stores or holds the pressure reading so that logger 10 can read the signal even when a pressure sensor is not activated (e.g., when an excitation voltage is turned off). Unit 43 is responsive to timing signals from a timer 47 to which it is coupled. While PAU 40 serves to process the pressure signal, the pH signal 44 is fed straight through so that system 2 can monitor the pH without having probe 30 disconnected.

Timer 47, which includes automatic power down features to conserve battery life, is also coupled to a voltage regulation unit 46. Voltage regulation unit 46, which is powered with a battery 49, maintains a constant DC voltage for system 2. Unit 46 detects low battery conditions and notifies the operator. The system is preferably battery powered to make it portable and to increase patient safety. Unit 46 also provides a switched excitation voltage 48 for a pressure transducer (described hereinbelow as an alternative embodiment).

AN ALTERNATIVE EMBODIMENT

Figure 5A:
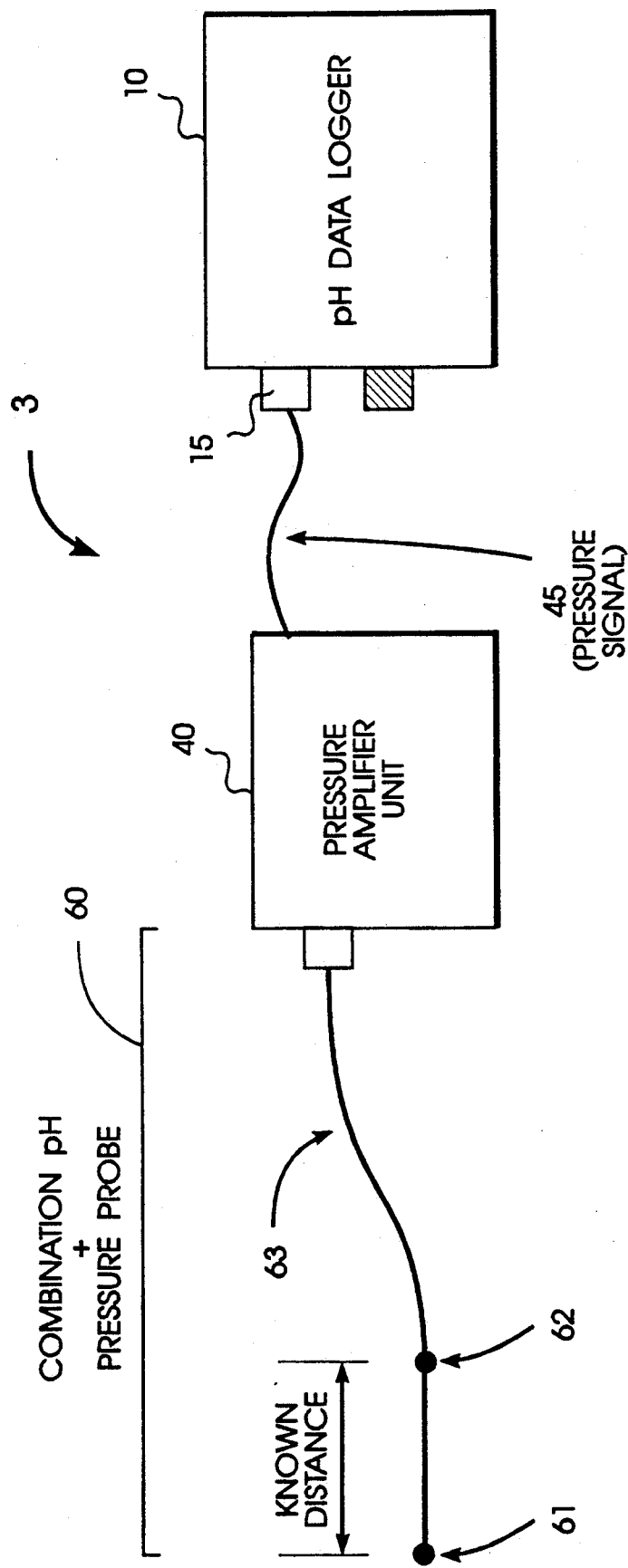
FIGS. 5A-5B are block diagrams illustrating a second ambulatory reflux monitoring device constructed in accordance with the principles of the present invention, where a pressure transducer is employed to measure pressure.
Figure 5B:
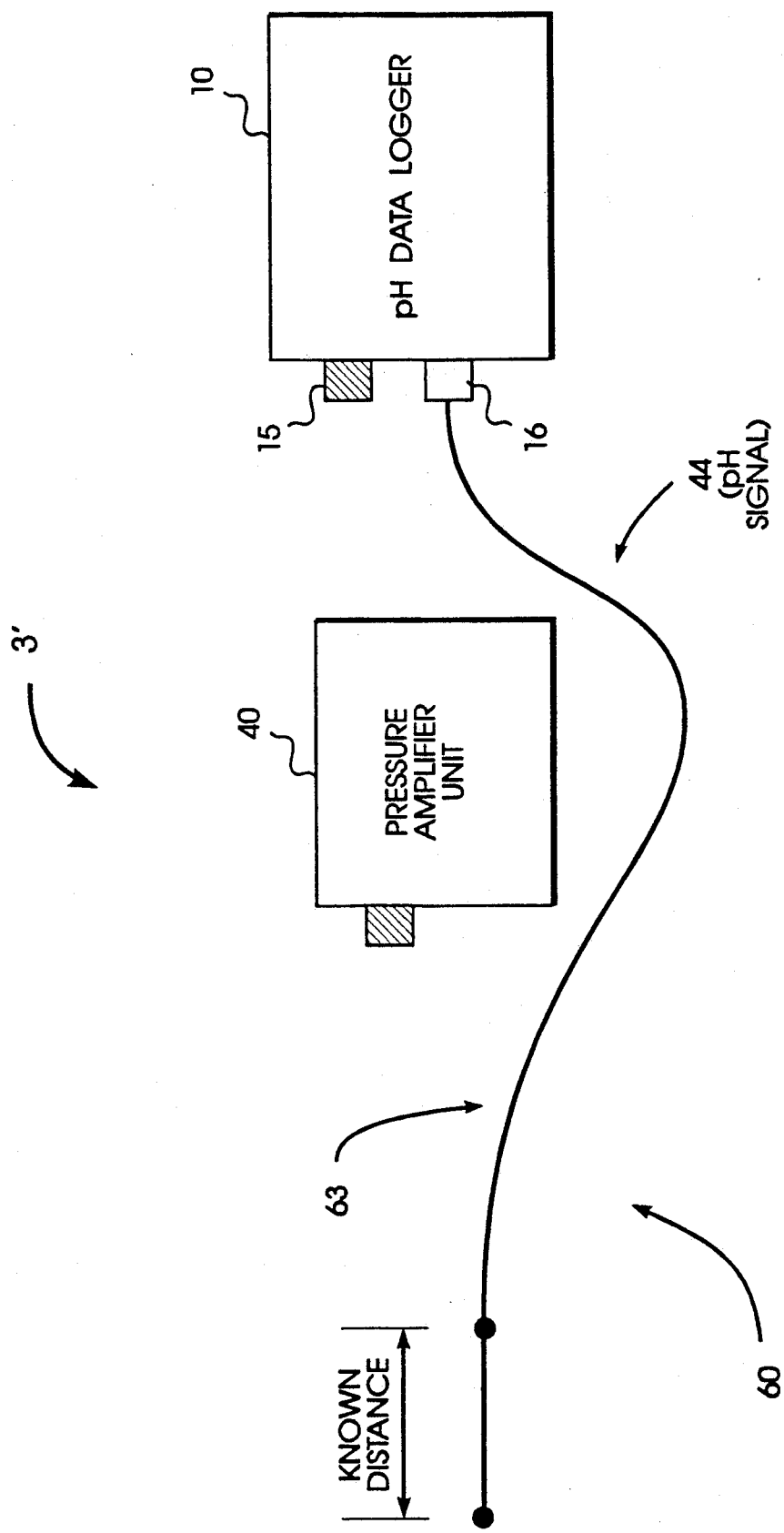

An alternative embodiment constructed in accordance with the principles of the present invention is a system where probe 20 includes a combination pH and a solid state pressure probe. Referring to FIGS. 5A-5B, this alternative embodiment is illustrated. System 3 provides a combination pH and pressure (transducer) probe 60 which is selectively coupled to pressure amplifier unit 40. Combination pH and pressure probe 60 includes a flexible tube 63 having a pH probe 61 and a pressure probe 62. As illustrated, pH probe 61 is coupled or secured to the distal tip of flexible tube 63 and generates pH signals in response to relative hydrogen ion concentrations. At a known distance proximal to this, pressure probe 62 is secured to member 63. Probe 62 transmits phasic pressure signals in response to pressure changes. Member 63 contains distance markings for easy assessment of depth. Combination probe 60 is similar in design to Konigsberg Motility Probe, Model P32-301B (Konigsberg Instruments, Pasadena, Calif.).

More particularly, for the LES locator 60, only one pressure transducer 62 is used in combination with an antimony pH measure tip 61 giving probe 60 a distal tip with a diameter of about 4.5 millimeters. Proximal to pressure transducer 62, the probe narrows to a diameter of about 2.5 millimeters, making it more tolerable for long term intubation.

The pressure output from probe 60 is received by PAU 40. After conditioning the signal (as set forth above) the pressure signal is transmitted via line 45 to port 15 of logger 10. As illustrated in FIG. 5A, system 3 is properly configured to locate the LES.

Referring now to FIG. 5B, an alternative configuration (system 3') is illustrated. After proper location of the LES (and hence a particular height above the LES), the proximal end of flexible tube 63 is detached from port 15 and coupled to port 16, thus decoupling PAU 40 from the system. In this configuration, logger 10 is ready to receive a pH signal 44 from the proximal end of member 63. Since PAU 40 is no longer required, system 3' is a portable unit including a properly positioned combination probe 60 and a logger 10.

A PREFERRED METHOD FOR REFLUX MONITORING

Figure 6A:
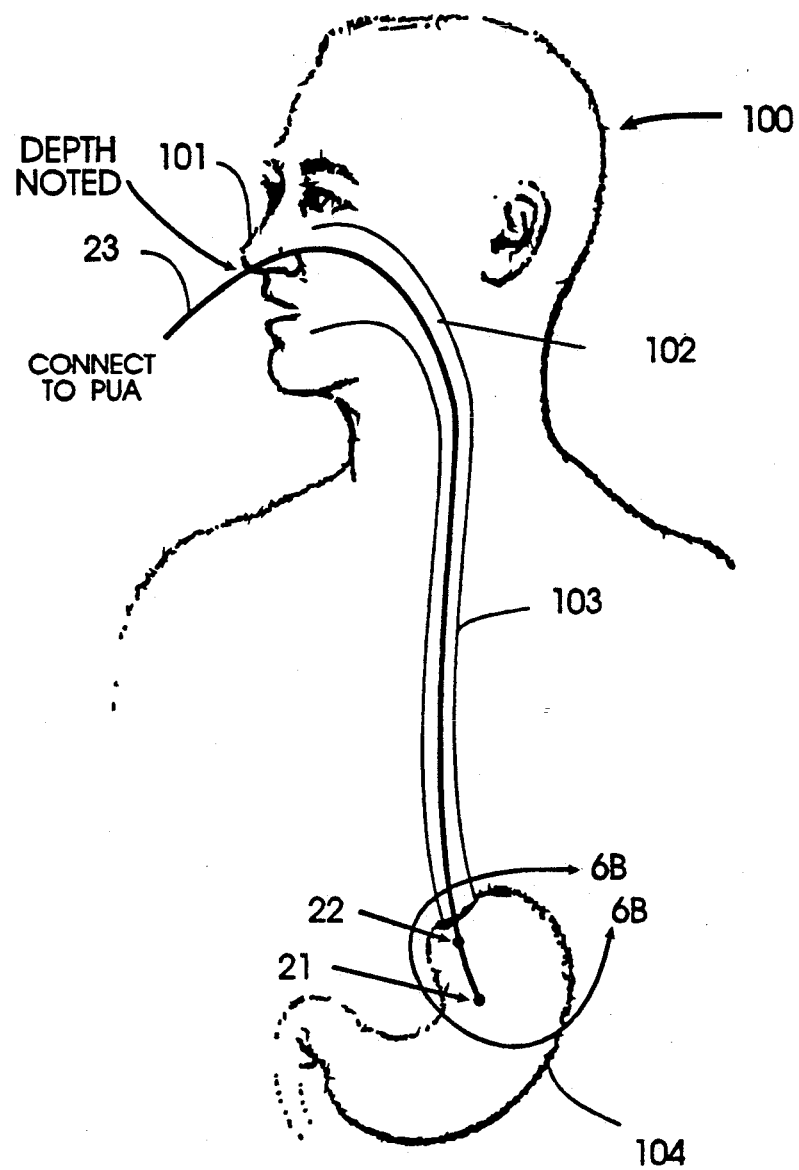
FIGS. 6A-6D illustrate a method as taught by the present invention for monitoring gastric acid reflux in a patient.

With reference to FIGS. 6A-D, a preferred method for monitoring reflux in a patient includes the following steps. In FIG. 6A, the free end (probe 21) of flexible tube 23 is inserted into the nose (or mouth) of a patient 100 and forwardly advance through the pharynx 102 and esophagus 103 until pressure sensor 22 is located within the lumen of the stomach 104. This location may be confirmed by low pH reading from probe 21, by the depth of the probe, and/or by pressure readings from probe 22. Before or after intubation, the proximal end of tube 23 is connected to external pressure transducer 50 (for infusion probes) or directly to pressure amplifier unit 40 (for pressure transducers).

The system is activated, for example, by selecting a pressure measure routine from display 11 with keypad 12. Since only relative pressures are important, the operator is prompted on display 11 to zero the offset by using offset adjustment unit 41. Next, while observing display 11, the operator slowly withdraws flexible tube 23 from the patient 100. The phasic pressures appear on display 11. The operator may adjust the refresh rate for optimum viewing.

Locating the LES by observing the LES respiration phasic pressures requires further explanation. It is known that the location of the LES corresponds to the junction of the esophagus with diaphragm, i.e., the LES is effectively co-planar with the diaphragm. With each inhalation, the diaphragm pushes down into the abdomen creating a partial vacuum in the chest cavity. At the same time, the intra-abdominal pressure rises slightly. With exhalation, the process reverses. By monitoring relative pressure changes instead of mean pressure, the junction of the diaphragm and the esophagus can be determined, thus determining the LES location. This technique is particularly useful for patients with LES incompetence.

Figure 6B:
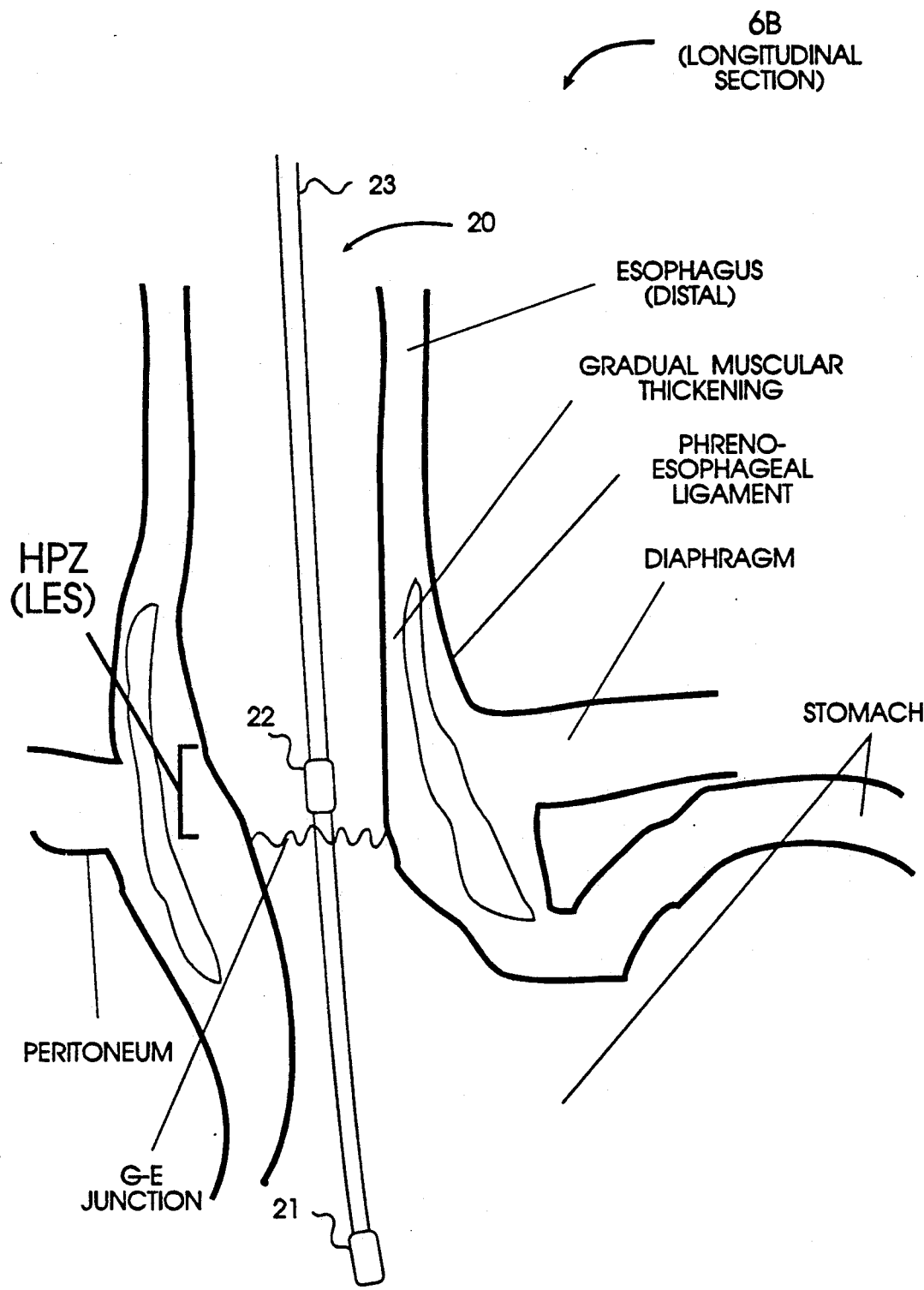

Referring to FIG. 6B (a longitudinal section through 6B of FIG. 6A), the placement of probe 20 within the body at this point is illustrated. Upon withdrawal of tube 23, probe 22 has entered the HPZ; probe 21 remains in the stomach 104. The LES respiration phasic pressure is continually monitored.

As illustrated, probe 22 is located at the LES when probe 22 reaches the plane of the diaphragm. Here, probe 22 is located at a "reversal point" or pressure inversion point for the LES respiration phasic pressure. Below (inferior to) the reversal point, ambient pressure increases with inhalation and decreases with expiration. Above (superior to) the reversal point, the opposite occurs. By observing display 11 and the patient's respirations, the operator can precisely determine this location and, hence, the LES.

Figure 6C:
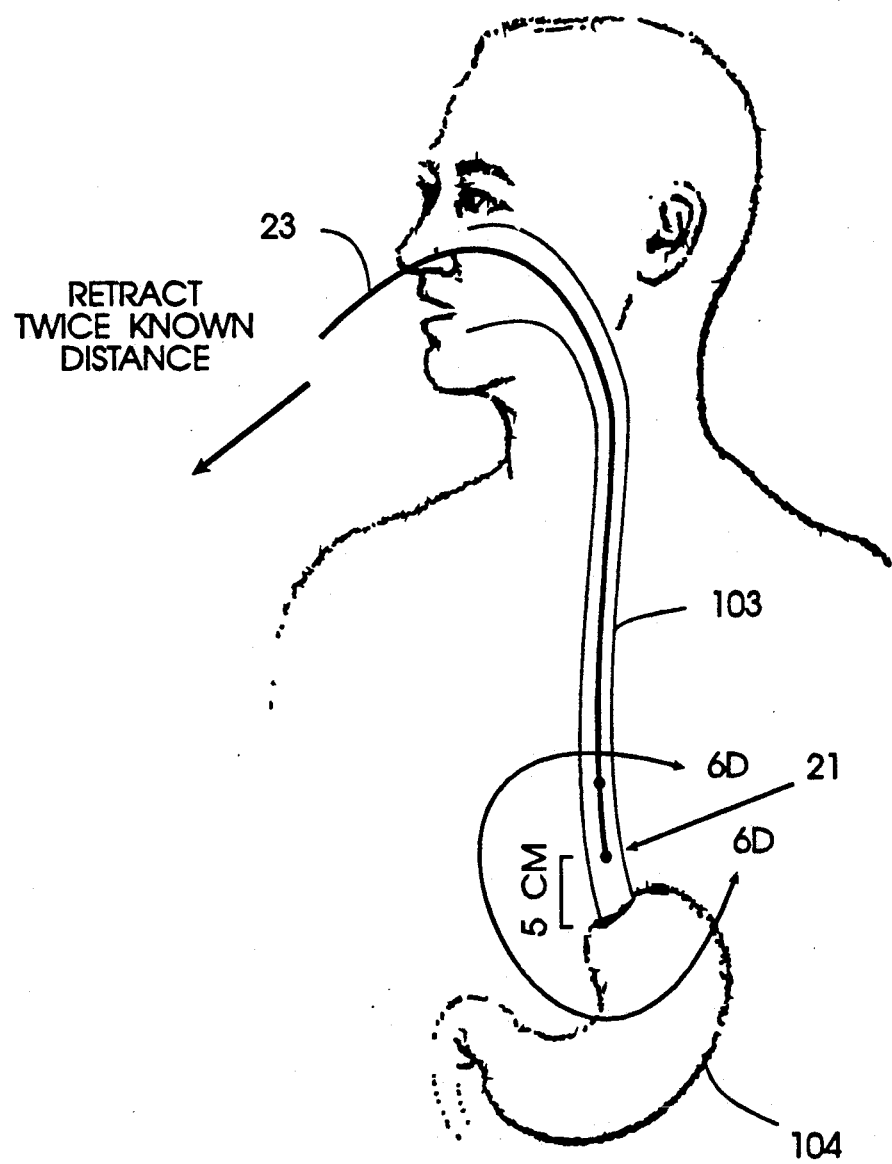

Upon locating the LES, the depth of flexible tube 23 is noted by reading distance markings at the patient's nose 101 (for nasal intubation) or teeth (for oral intubation). As illustrated in FIG. 6C, flexible tube 23 is then withdrawn from the patient 100 until pH probe 21 is located a known distance above the LES. In a preferred method, probe 21 is located 5 cm above the LES.

Figure 6D:
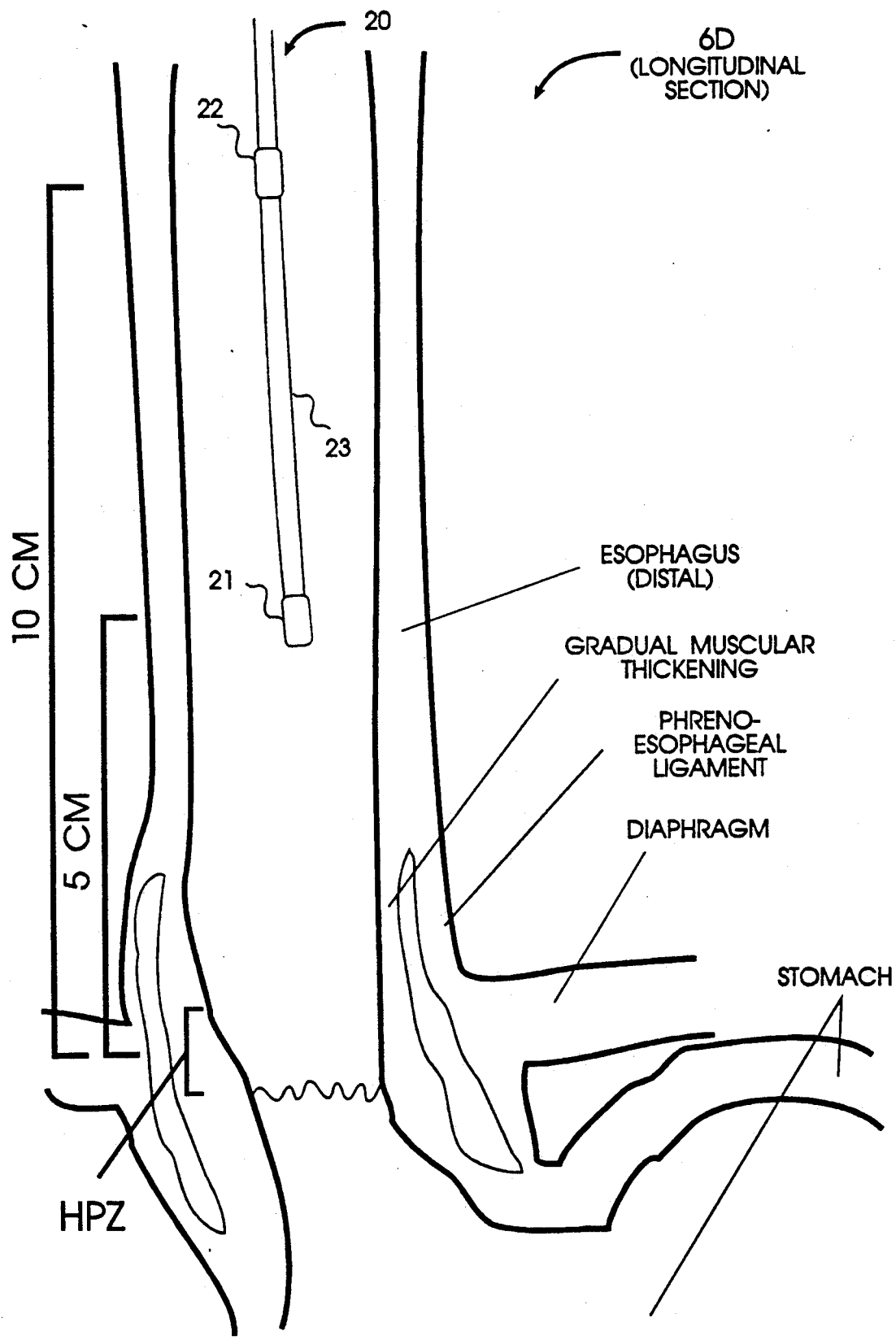

Referring to FIG. 6D (a longitudinal section through 6D of FIG. 6C), the placement of probe 20 within the body at this point is illustrated. Pressure sensor 22 has been moved cranially (towards the head) by a predetermined distance. If probe 22 is located 5 cm above probe 21 and probe 22 is at the LES, tube 23 must be withdrawn 10 centimeters (5 cm for probe-probe distance and 5 cm for height above LES) for probe 21 to lie 5 cm above the LES. While any set of known distances may be employed, a preferred method is to use multiples of 5 cm (e.g., 5 and 10 cm) since operators are used to working with this unit.

After positioning probe 21 a known distance above the LES, tube 23 is secured to the patient 100 using adhesive or umbilical tape. Next, probe 20 is disconnected from PAU 40 (or external pressure transducer 50) and connected directly to logger 10. Since logger 10 is portable, the patient is free to ambulate. Serial pH measurements are recorded over a 24 hour period. At the conclusion of this study, probe 20 and logger 10 are removed from the patient. The patient data are retrieved from logger 10.

PATIENT DATA

The accurate location of the lower esophageal sphincter (LES) prior to pHmetry is often cumbersome and at times frustrating. The usual approach includes doing a standard pull-through technique manometric study using the respiratory pressure inversion point (PIP) to identify the proximal extent of the LES followed by reintubating with the pH probe. A second simpler, yet less accurate pH withdrawal technique has also been used.

The following study is offered for purposes of illustration and not limitation. Ten subjects were studied using the preferred technique to locate the LES with a single intubation. A standard pH probe with an internal reference was attached to a 1 mm diameter tube with a single orifice for pressure recording 5 cm proximal to the pH electrode (Zinetics Medical, Salt Lake City, Utah). The diameter of this assembly was 3 mm compared to the standard 2 mm pH probe. The catheter was advanced to the stomach and then withdrawn at 1 cm increments. After recording quiet breathing, the subjects were asked to inspire deeply at each station. This was continued until both the manometric and pH defined endpoints were determined. End points included: Negative pressure with deep inspiration, PIP, and point of pH increase ($>4$).

The following results were obtained. The combined probe allowed identification of the PIP during quiet respirations; pH change deviated by $>1$ cm in 75% of subjects. The use of deep inspiration was an excellent qualitative indicator of PIP with 11/14 subjects having PIP identical to the point where inspiration was all negative and 3/14 having only 1 cm deviation.

These preliminary studies suggest that this simplified technique can localize LES for pH probe placement using a single intubation while providing more accurate placement than the pH change method.

While the invention is described in some detail with specific reference to a single preferred embodiment and certain alternatives, there is no intent to limit the invention to that particular embodiment or those specific alternatives. The true scope of the invention is defined not by the foregoing description but by the following claims.

What is claimed is:

1. A system for monitoring gastric acid reflux in a patient comprising:
   a combination probe, having a distal location and a proximal location, comprising a flexible tube having a pH sensor point at the distal location and a pressure sensor point at the proximal location;
   means, operably coupled to said pH sensor point, for generating pH signals in response to a hydrogen ion concentration thereat;
   means, operably coupled to said pressure sensor point, for generating pressure signals in response to phasic pressure changes thereat;
   said pressure signal generating means including an infusion pump coupled to a source of liquid and an infusion probe coupled to the infusion pump, the infusion probe disposed proximally on said combination probe from said pH sensor point for delivering the liquid from the infusion pump, the infusion probe including an exit opening at said proximal location so that variations in the phasic pressure changes at said proximal location are transmitted through the flowing liquid to permit generation of said pressure signals;
   a display means, coupled to said pressure signal generating means, for providing information for positioning said pH sensor point in response to said pressure signals; and
   a memory means, coupled to said pH signal generating means, for storing said pH signals.

2. The system of claim 1, wherein said pH sensor point and said pressure sensor point are located a known distance apart.

3. The system of claim 2, wherein said known distance is 5 cm.

4. The system of claim 1, wherein said combination probe is a single channel probe.

5. The system of claim 1, wherein said flexible tube includes distance markings for determining depth.

6. The system of claim 1, wherein said pH signal generating means comprises a pH probe coupled to a collinear line.

7. The system of claim 6, wherein said pH probe is an antimony pH measure tip having a diameter substantially equal to 4.5 mm.

8. The system of claim 6, wherein said pH probe is a bulb-type pH probe.

9. The system of claim 1, wherein said pressure signal generating means further comprises:
an external pressure transducer, selectively coupled to said infusion probe, for generating pressure signals in response to a back pressure from said column of water;
a pressure amplifier means, coupled to said external pressure transducer, for conditioning said pressure signals; a microprocessor, selectively coupled to said pressure amplifier means, for receiving said pressure signals from said pressure amplifier means; and
a program, operably coupled to said microprocessor, for instructing said microprocessor to detect said pressure signals.

10. The system of claim 9, wherein said pressure amplifier means comprises:
an amplification means for amplifying said pressure signals;
an offset adjustment means, coupled to said amplification means, for adjusting said amplification means;
a sample and hold means, coupled to said amplification means, for temporarily storing said pressure signals in response to a timing signal from a timer; and
a voltage regulation means, coupled to said timer, for regulating voltage for said system.

11. The system of claim 1, wherein said memory means is a random access memory (RAM).

12. The system of claim 1, wherein said display means is a liquid crystal display (LCD).

13. The system of claim 1, further comprising a communication port for transmitting said stored pH signals to another system.

14. A method for monitoring gastric acid reflux at a certain position above the lower esophageal sphincter (LES) of a patient, said method comprising:
(a) selecting a combination probe, having a distal location and a proximal location, said combination probe including a flexible tube having a pH sensor point at the distal location and a pressure sensor point at the proximal location, said pH sensor point being operably coupled to means for generating pH signals in response to a hydrogen ion concentration thereof, and said pressure sensor point being operably coupled to means for generating pressure signals in response to phasic pressure changes generated by the diaphragm of the patient;
(b) inserting said distal location of said combination probe into a selected one of the nose or the mouth of the patient;
(c) forwardly advancing said combination probe until said pressure sensor point lies within the stomach of the patient;
(d) positioning said pressure sensor point at the LES by
observing respirations of the patient,
observing said pressure signals, and
withdrawing said combination probe until said observed pressure signals reverse in relation to said respirations;
(e) positioning said pH sensor point at said certain position above the LES by withdrawing said combination probe a known distance; and
(f) recording said pH signals.

15. The method of claim 14, wherein step (e) comprises:
positioning said pH sensor point at said certain position above the LES by withdrawing said combination probe a distance equal to 10 cm.

16. The method of claim 14, wherein before step (d), further comprises the step of:
(g) confirming placement of said pressure sensor point within the stomach by
observing said pH signals for low pH values, and
observing said pressure signals for low pressure values.

17. The method of claim 14, wherein said withdrawing said combination probe step comprises:
withdrawing said combination probe until said observed pressure signals reverse in relation to said respirations, thereby placing said pressure sensor point at the location of the LES which is co-planar with the diaphragm of the patient.

* * * * *